US00PP29014P3

(12) United States Plant Patent
Danziger

(10) Patent No.: US PP29,014 P3
(45) Date of Patent: Feb. 27, 2018

(54) ***VERBENA* PLANT NAMED 'DVERDEPINK'**

(50) Latin Name: *Verbena hybrida*
Varietal Denomination: DVERDEPINK

(71) Applicant: Gavriel Danziger, Beit Dagan (IL)

(72) Inventor: Gavriel Danziger, Beit Dagan (IL)

(73) Assignee: Danziger 'DAN' Flower Farm (IL)

( * ) Notice: Subject to any disclaimer, the term of this patent is extended or adjusted under 35 U.S.C. 154(b) by 37 days.

(21) Appl. No.: 14/999,425

(22) Filed: May 3, 2016

(65) Prior Publication Data

US 2017/0325378 P1 Nov. 9, 2017

(51) Int. Cl.
*A01H 5/02* (2006.01)

(52) U.S. Cl.
USPC ..... Plt./308

CPC ..... *A01H 5/02* (2013.01)

(58) Field of Classification Search
USPC ..... Plt./308
See application file for complete search history.

(56) References Cited

PUBLICATIONS

Drotleff, Greenhouse Growers, Apr. 21, 2015.*
UPOV Record Detail 'DVERDEPINK', 2016.*

* cited by examiner

*Primary Examiner* — Keith O Robinson
(74) *Attorney, Agent, or Firm* — Cassandra Bright

(57) ABSTRACT

A new and distinct *Verbena* cultivar named 'DVERDEPINK' is disclosed, characterized by early flowering, an abundance of pink flowers, semi-trailing habit and tolerance to powdery mildew. The new variety is a *Verbena*, normally produced as an outdoor garden or container plant.

2 Drawing Sheets

Figure 1:
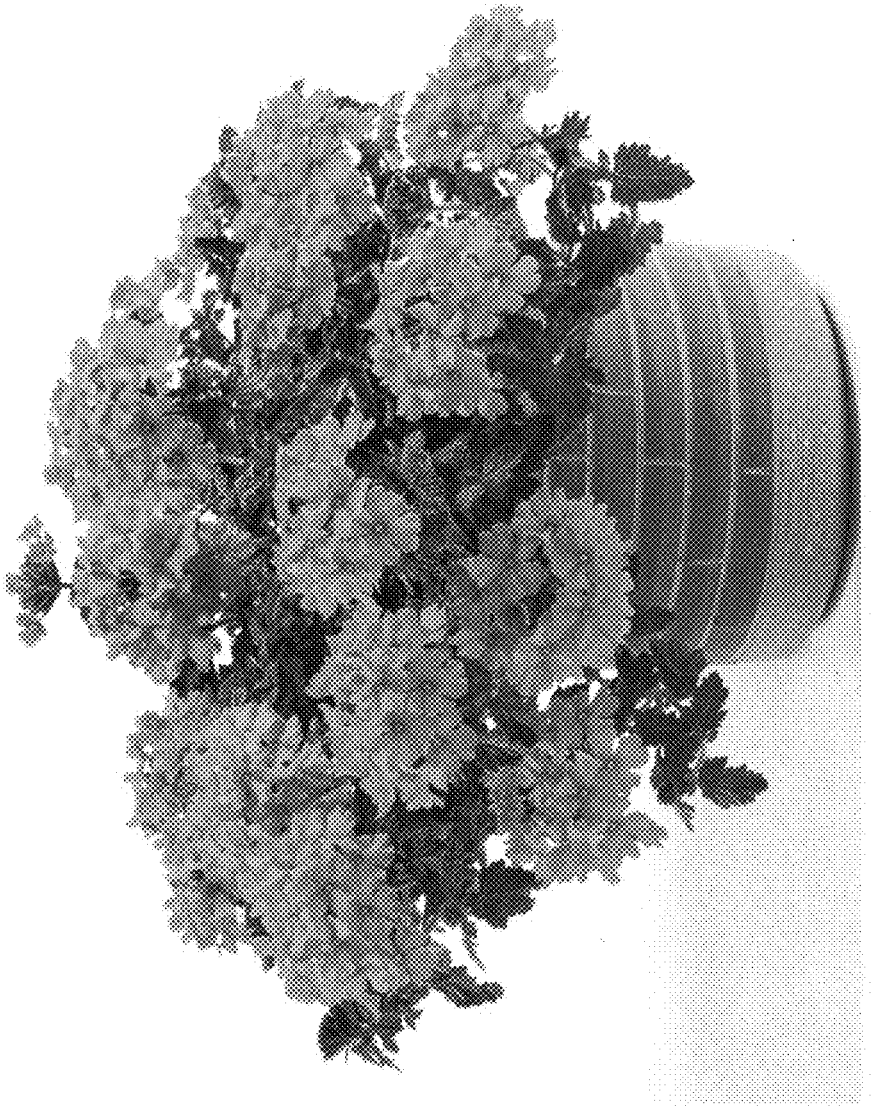

Latin name of the genus and species: *Verbena hybrida.*
Variety denomination: 'DVERDEPINK'.

BACKGROUND OF THE INVENTION

The new *Verbena* cultivar is a product of a planned breeding program conducted by the inventor, Gavriel Danziger in Moshav Mishmar Hashiva, Israel. The objective of the breeding program was to produce new *Verbena* varieties. The cross resulting in this new variety was made during July of 2011.

The seed parent is the, unpatented, propriety variety referred to as *Verbena* 'VE-11-3996'. The pollen parent is the, unpatented, propriety variety referred to as *Verbena* 'VE-10-3695'. The new variety was discovered in December of 2012 by the inventor in a group of seedlings resulting from the 2011 crossing, in a greenhouse in Moshav Mishmar Hashiva, Israel.

Asexual reproduction of the new cultivar 'DVERDEPINK' first by vegetative cuttings was first performed during the March of 2013, at a greenhouse in Moshav Mishmar Hashiva, Israel. Subsequent propagation by vegetative cuttings has shown that the unique features of this cultivar are stable and reproduced true to type in multiple successive generations.

SUMMARY OF THE INVENTION

The cultivar 'DVERDEPINK' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DVERDEPINK'. These characteristics in combination distinguish 'DVERDEPINK' as a new and distinct *Verbena* cultivar:

1. Plants begin to flower early.
2. Semi trailing habit.
3. Tolerant to powdery mildew.
4. Highly floriferous plants.
5. Plants with an abundance of pink flowers.

PARENT COMPARISON

Plants of the new cultivar 'DVERDEPINK' are similar to plants of the seed parent, *Verbena* 'VE-11-3996', in most horticultural characteristics, however, plants of the new cultivar 'DVERDEPINK' differ in the following;

1. The new variety has pink flowers, whereas the seed parent has flowers that are light pink with a dark pink center.
2. The new variety is tolerant to powdery mildew, whereas the seed parent is sensitive to powdery mildew.
3. The new variety is a more vigorous than the seed parent which has a weaker growing habit.

Plants of the new cultivar 'DVERDEPINK' are similar to plants of the pollen parent, *Verbena* 'VE-10-3695', in most horticultural characteristics, however, plants of the new cultivar 'DVERDEPINK' differ in the following;

1. The new variety has pink flowers, whereas the pollen parent has bi-color magenta and white flowers.
2. The new variety has a semi-trailing habit, whereas the pollen parent has a fully trailing plant habit.
3. Foliage of the pollen parent turns yellow in low temperatures, whereas the new variety is tolerates low temperatures without foliar color change.

COMMERCIAL COMPARISON

Plants of the new cultivar 'DVERDEPINK' can be compared to the unpatented commercial variety *Verbena* 'Empress Flair Cherry Charme'. These varieties are similar in most horticultural characteristics; however, 'DVERDEPINK' differs in the following:

1. Flower color of the comparator is dark pink with white center, while flower color of the new variety is pink.
2. The new variety has smaller foliage.
3. The new variety has smaller flowers.

Plants of the new cultivar 'DVERDEPINK' can also be compared to the unpatented commercial variety *Verbena* 'Vera Rose'. These varieties are similar in most horticultural characteristics; however, 'DVERDEPINK' differs in the following:

1. The new variety has larger flowers than the comparator.
2. The new variety has a pink flower whereas the comparator has a dark pink flower.
3. The new variety has broad foliage, whereas the comparator has thin lacy foliage.

BRIEF DESCRIPTION OF THE PHOTOGRAPHS

The accompanying photograph in FIG. 1 illustrates in full color a typical plant of 'DVERDEPINK' grown in in a greenhouse, in Moshav Mishmar Hashiva, Israel.

Figure 2:
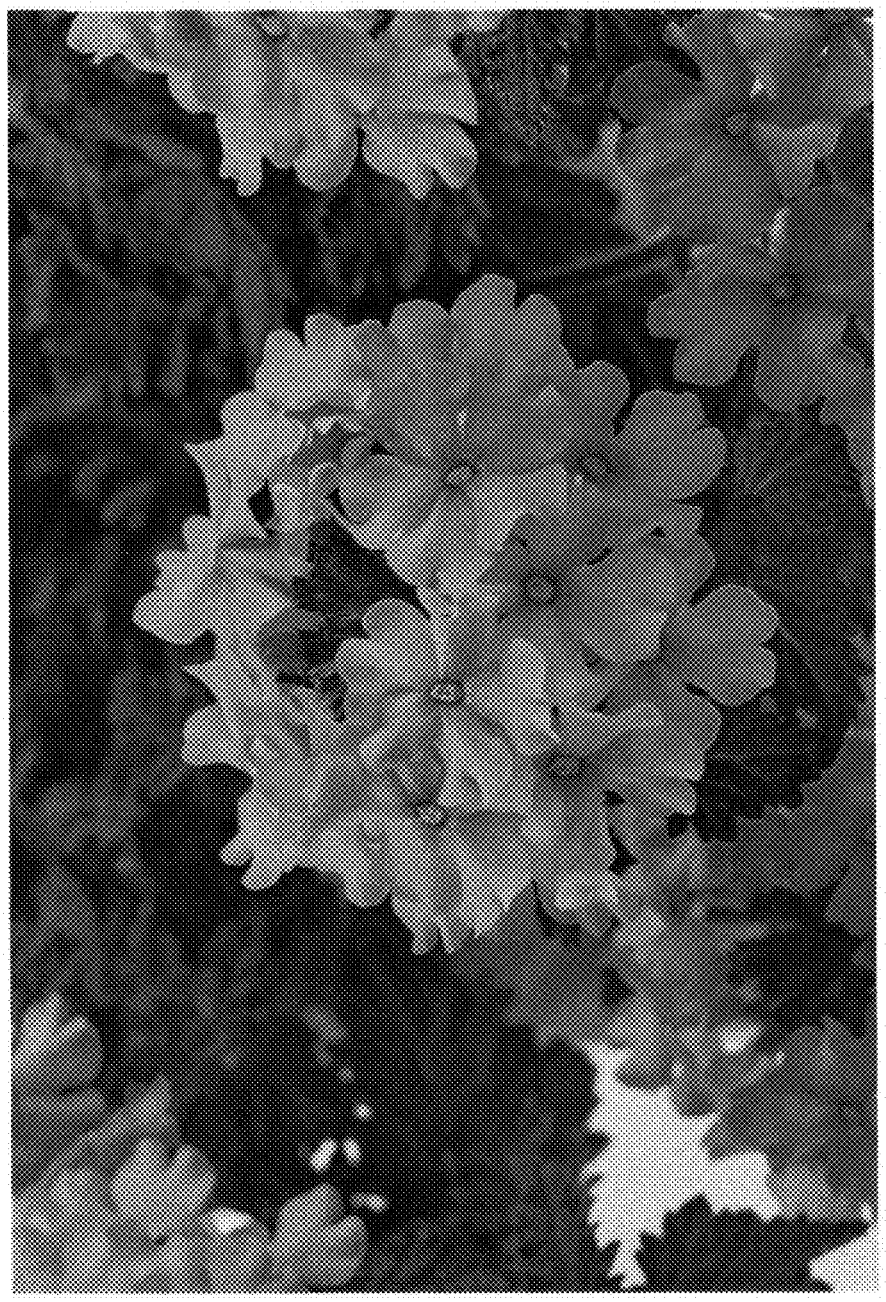

FIG. 2 illustrates in full color a typical inflorescence of 'DVERDEPINK'. Age of the plant photographed is approximately 9 weeks from a rooted cutting in a 12 cm pot.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DVERDEPINK' plants grown in a nursery in Moshav Mishmar Hashiva, Israel, under natural lighting. Measurements were taken during Autumn of 2015. The plants were approximately 80 days from a rooted cutting in a 12 cm pot. The growing temperature ranged from 18° C. to 27° C. during the days, 10° C. to 15° C. during the nights. Measurements and numerical values represent averages of typical plant types.

Botanical classification: *Verbena hybrida* 'DVERDEPINK'.

PROPAGATION

Time to initiate roots: 7 to 9 days at optimal temperature of approximately 25 degree C.

Root description: Fibrous.

PLANT

Growth habit: Semi Trailing.

Pot size of plant described: 12 cm.

Height: 12 cm.

Plant spread: 45 cm.

Growth rate: Fast.

Branching characteristics: Freely branching.

Length of primary lateral branches: 27 cm.

Diameter of lateral branches: 0.3 cm.

Quantity of primary lateral branches: Approximately 8.

Characteristics of primary lateral branches:

*Form.*—Cylindrical.

*Diameter.*—0.3 cm.

*Color.*—Near Yellow-green 144A.

*Texture.*—Pubescent.

*Strength.*—Flexible.

*Anthocyanin coloration.*—Not present.

Internode length: 2 cm.

FOLIAGE

Leaf:

*Arrangement.*—Opposite.

*Quantity.*—Approximately 25 per branch.

*Average length.*—3.5 cm.

*Average width.*—2.2 cm.

*Shape of blade.*—Deltoid. Shallow lobes, 3 to 7 per leaf, about 2 to 3 mm deep.

*Apex.*—Acute.

*Base.*—Rounded.

*Margin.*—Crenate, Irregular.

*Texture of top surface.*—Pubescent.

*Texture of bottom surface.*—Pubescent.

*Pubescence.*—Strigose.

*Aspect.*—Mainly flat, attached at approximately 45 degrees.

*Color.*—Young foliage upper side: Near Green RHS 138 A. Young foliage under side: Near Green RHS 138 B. Mature foliage upper side: Near Green RHS N137 B. Mature foliage under side: Near Green RHS 137 C.

*Venation.*—Type: Pinnate. Venation color upper side: Near Yellow-green RHS 145 B. Venation color under side: Near Yellow-green RHS 145 C.

*Petiole.*—Length: 0.5 cm. Diameter: 0.2 cm. Color: Near Yellow-green RHS 145 B. Texture: Pubescent.

FLOWER

Natural flowering season: Spring to Autumn under conditions found in Beit Dagan, Israel.

Days to flowering from rooted cutting: 16 to 21 Days.

Inflorescence and flower type and habit: Terminal cluster.

Inflorescence size: 5 to 6 cm diameter.

Rate of flower opening: 4 to 6 days from bud to fully opened flower.

Flower longevity on plant: 5 to 8 Days.

Persistent or self-cleaning: Self-Cleaning.

Bud:

*Shape.*—Quinquangular.

*Length.*—0.8 cm.

*Diameter.*—0.2 cm.

*Color.*—Near Green RHS 138 A.

Corolla:

*Flower.*—Depth: 2.5 cm. Diameter: 2 cm. Petals/lobes: Number: 5. Arrangement: Radial, touching. Aspect: Somewhat recurved. Length: 1.0 cm. Width: 1.0 cm. Shape: Obcordate. Aspect: upright. Margin: Entire. Texture: Smooth.

*Color.*—When opening: Upper surface: Near Red-purple N57 C. Lower surface: Near Red-purple 62 B. Fully opened: Upper surface: Near Red-purple N66 C. Lower surface: Near Red-purple 62 B.

*Throat*.—Color: Near Yellow 2 C. Texture: Smooth. Tube color: Near Yellow-green 149 D. Tube length: About 1.7 cm. Corolla Eye: Not present.

Calyx:

*Form*.—Tubular.

*Length*.—1 cm.

*Diameter*.—0.1 cm.

*Sepal shape*.—Five sepals whose margins are fused-quinquangular.

*Sepal margin*.—Entire.

*Sepal texture*.—Pubescent, all surfaces.

*Sepal color*.—Upper surface: Near Yellow-green 146 C. Lower surface: Near Yellow-green 145 B.

Pedicels:

*Length*.—2.5 cm.

*Diameter*.—0.2 cm.

*Color*.—Near Yellow-green 146 C.

*Texture*.—Pubescent.

Fragrance: None.

REPRODUCTIVE ORGANS

Stamens:

*Number* (*per flower*).—4.

*Filament length*.—0.2 cm.

*Anthers*.—Shape: Conical. Length: 0.1 cm. Color: Near Yellow-Green 154 B.

Pollen:

*Color*.—Near Green-Yellow 1A.

*Amount*.—Abundant.

Pistils:

*Quantity per flower*.—1.

*Length*.—2 cm.

*Styles*.—Length: 2 cm.

*Color*.—Near Green-Yellow 1 C.

*Stigma*.—Shape: Ovoid.

*Color*.—Near Yellow-Green 145 A.

OTHER CHARACTERISTICS

Seeds and fruits: Low quantity of seeds produced. Minute, elliptic shaped, dry to nearly papery. Brown, not accurately measured by R.H.S. chart, due to size.

Disease/pest resistance: Tolerant of powdery mildew. Typical pathogens of powdery mildew include the fungi *Golovinomyces, Leveillula*, and *Microsphaera*. Neither resistance nor susceptibility to additional typical diseases and pests of *Verbena* has been observed to date.

Temperature tolerance: Tolerates temperatures from approximately −1° C. to 32° C.

What is claimed is:

1. A new and distinct cultivar of *Verbena* plant named 'DVERDEPINK' as herein illustrated and described.

* * * * *